United States Patent
Butler et al.

(10) Patent No.: US 8,636,771 B2
(45) Date of Patent: Jan. 28, 2014

(54) SPINAL IMPLANTS FOR LUMBAR VERTEBRA TO SACRUM FIXATION

(75) Inventors: Michael S. Butler, St. Charles, IL (US); Daniel Predick, Chicago, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 19 days.

(21) Appl. No.: 13/306,744

(22) Filed: Nov. 29, 2011

(65) Prior Publication Data
US 2012/0136390 A1    May 31, 2012

Related U.S. Application Data

(60) Provisional application No. 61/417,484, filed on Nov. 29, 2010.

(51) Int. Cl.
*A61B 17/70* (2006.01)
(52) U.S. Cl.
USPC .......................... 606/248; 606/247; 606/249
(58) Field of Classification Search
USPC ................. 606/279, 297, 248, 249, 246, 247; 623/17.11–17.16
See application file for complete search history.

(56) References Cited

U.S. PATENT DOCUMENTS

| | | | |
|---|---|---|---|
| 4,466,426 A | 8/1984 | Blackman | |
| 5,645,599 A | 7/1997 | Samani | |
| 7,048,736 B2 * | 5/2006 | Robinson et al. | 606/86 B |
| 8,048,117 B2 | 11/2011 | Zucherman | |
| 8,231,656 B2 | 7/2012 | Lee et al. | |
| 8,241,330 B2 * | 8/2012 | Lamborne et al. | 606/248 |
| 8,343,190 B1 * | 1/2013 | Mueller et al. | 606/248 |
| 8,382,801 B2 * | 2/2013 | Lamborne et al. | 606/248 |
| 2003/0040746 A1 * | 2/2003 | Mitchell et al. | 606/61 |
| 2003/0236520 A1 | 12/2003 | Lim et al. | |
| 2005/0222681 A1 | 10/2005 | Richley et al. | |
| 2005/0261769 A1 | 11/2005 | Moskowitz et al. | |
| 2005/0278036 A1 | 12/2005 | Leonard et al. | |
| 2006/0084988 A1 | 4/2006 | Kim | |
| 2006/0089718 A1 | 4/2006 | Zucherman et al. | |
| 2006/0241601 A1 | 10/2006 | Trautwein et al. | |
| 2008/0114456 A1 | 5/2008 | Dewey et al. | |
| 2008/0312741 A1 | 12/2008 | Lee et al. | |
| 2009/0062915 A1 * | 3/2009 | Kohm et al. | 623/17.11 |
| 2011/0022090 A1 | 1/2011 | Gordon et al. | |
| 2011/0066186 A1 | 3/2011 | Boyer et al. | |
| 2011/0144692 A1 | 6/2011 | Saladin et al. | |
| 2011/0172709 A1 | 7/2011 | Lyons et al. | |
| 2011/0184468 A1 | 7/2011 | Metcalf et al. | |
| 2012/0016418 A1 * | 1/2012 | Chin et al. | 606/249 |
| 2012/0109203 A1 * | 5/2012 | Dryer et al. | 606/249 |

\* cited by examiner

*Primary Examiner* — Pedro Philogene
(74) *Attorney, Agent, or Firm* — Foley & Lardner LLP

(57) ABSTRACT

A spinal implant is provided for posterior vertebral stabilization and/or fixation of a lumbar vertebra relative to the pelvis by attachment to the spinous process of a lumbar vertebra and to the sacrum of the pelvis. The posterior spinal implant has a spinous process attachment portion and a sacrum attachment portion formed by a first part having a first spinous process segment and a first sacrum segment and a second part having a second spinous process segment and a second sacrum segment. The first segments are carried on a first arm, while the second segments are carried on a second arm with the first and second arms adjustable relative to each other. The first and second spinous process segments and the first and second sacrum segments each have a plurality of inwardly extending spikes for respectively gripping or clamping against the sides of the spinous process and the sacrum.

17 Claims, 16 Drawing Sheets

SPINAL IMPLANTS FOR LUMBAR VERTEBRA TO SACRUM FIXATION

RELATED APPLICATIONS

This patent application claims the benefit of and/or priority under 35 U.S.C. §119(e) to U.S. Provisional Patent Application Ser. No. 61/417,484 filed Nov. 29, 2010, entitled "Spinal Implant For Lumbar Vertebra To Sacrum Fixation" the entire contents of which is specifically incorporated herein by this reference.

BACKGROUND OF THE INVENTION

1. Field of the Invention

The present invention relates to implants for the spine and, more particularly, to posterior spinal implants for lumbar vertebrae stabilization/fixation.

2. Background Information

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as spinal stenosis. Spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of spinal stenosis include leg pain ("pins and needles") that can limit standing, walking, self-supporting daily activities, work, social and recreational pursuits. Lack of activity because of spinal stenosis may lead to obesity, depression and general physical deterioration.

Spinal stenosis is one of the most common reason for back surgery in people over the age of 50 in the United States. While there are various non-surgical treatments for spinal stenosis, various spinal decompression surgical procedures may be utilized to reduce or eliminate the symptoms of spinal stenosis or other spinal problems. Such procedures include a laminectomy a laminotomy, a foraminotomy or a facetectonomy.

Another surgical treatment for spinal stenosis and other spinal problems is known that is less invasive than the above surgical procedures. This other surgical treatment involves implanting a device between bony projections of adjacent vertebrae, particularly, but not necessarily, between spinous processes of the adjacent vertebrae. This achieves interspinous process decompression for alleviating spinal stenosis and other spinal problems. However, when spinal decompression, fixation or stabilization is desired between a lower lumbar vertebrae and the pelvis, prior art interspinous process decompression implants do not work.

In view of the foregoing, it is therefore desirable to provide a spinal implant for interspinous decompression of lower lumbar vertebrae relative to the pelvis. Accordingly, there exists a need for a spinal implant that provides vertebral stabilization/fixation of a lumbar vertebra relative to the pelvis.

SUMMARY OF THE INVENTION

The present invention is a spinal implant for posterior vertebral stabilization and/or fixation of a lumbar vertebra relative to the pelvis. The present posterior spinal implant is particularly configured for attachment to the spinous process of a lumbar vertebra and to the sacrum of the pelvis.

The posterior spinal implant has a superior portion that is configured for attachment to the spinous process of a lumber vertebra and an inferior portion that is configured for attachment to the sacrum. Both the superior portion and the inferior portion are adjustable to allow for variations in individual bone anatomy.

In one form, the inferior portion of the present posterior spinal implant is formed by two, preferably flexible, tails each one of which is defined by a segmented band or strip that provides break points along its span for length adjustment. In this manner, each tail may be positioned and sized for fixation onto the sacrum. Additionally, each tail has a plurality of bores for receiving a bone screw to attach the tail to the sacrum. Preferably, but not necessarily, each segment of the tail has a bone screw bore in order to provide various attachment points along the length adjusted tail span.

The superior portion of this form has two titanium flanges each having a plurality of inwardly extending spikes for gripping or clamping against the sides of the spinous process. Additionally, one of the flanges is movable relative to the other flange to provide adjustability in clamping of the spinous process.

Moreover, in this form, the posterior spinal implant has a body formed as a barrel with a first transverse surface on one end of the barrel and having a first superior flange extending from the superior end of the first transverse surface and a first inferior tail as described above extending from the inferior end of the first surface for attachment to the sacrum. The first superior flange has a first plurality of spikes for engaging a first lateral side of the spinous process of a lumbar vertebra. A second transverse surface is movably carried on the barrel and has a second superior flange extending from the superior end of the second transverse surface and a second inferior tail as described above extending from the inferior end of the second transverse surface for attachment to the sacrum. The second superior flange has a second plurality of spikes for engaging a second lateral side of the spinous process of the lumbar vertebra. The second transverse surface may be fixed in position along the barrel by a fixation portion associated with the second transverse surface. In this manner, the second transverse surface and thus the second superior flange and the second inferior tail move in concert.

In another form, the posterior spinal implant has a superior or spinous process attachment portion and an inferior or sacrum attachment portion formed by a first part having a first spinous process segment of the spinous process attachment portion and a first sacrum segment of the sacrum attachment portion, and a second part having a second spinous process segment of the spinous process attachment portion and a second sacrum segment of the sacrum attachment portion. The first segments are carried on a first arm, while the second segments are carried on a second arm with the first and second arms adjustable relative to each other.

The first and second spinous process segments each have a plurality of inwardly extending spikes for gripping or clamping against the sides of the spinous process. The first and second sacrum segments each have a plurality of inwardly extending spikes for gripping or clamping against the nub of the first sacrum vertebra of the sacrum. Additionally, the first sacrum segment is angularly adjustable to provide greater variation in clamping of the sacrum. The angle of the first sacrum segment is also fixable.

Moreover, in this form, the first arm has a transverse projection that carries the second arm, the second arm being adjustable along the length of the projection. The second arm is fixable in position on the projection to provide clamping of the spinous process segments against the spinous process and of the sacrum segments against the sacrum.

In a variation of this embodiment the first and second sacrum segments each have a plurality of serrations or teeth that aid in gripping against the nub of the first sacrum vertebra.

The present posterior spinal implant is made from a biocompatible material that is preferably, but not necessarily, titanium.

BRIEF DESCRIPTION OF THE DRAWINGS

The above mentioned and other features, advantages and/ or objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non-discussed features may be inherent in component geometry and/or configuration.

DETAILED DESCRIPTION OF EMBODIMENTS OF THE INVENTION

Figure 1:
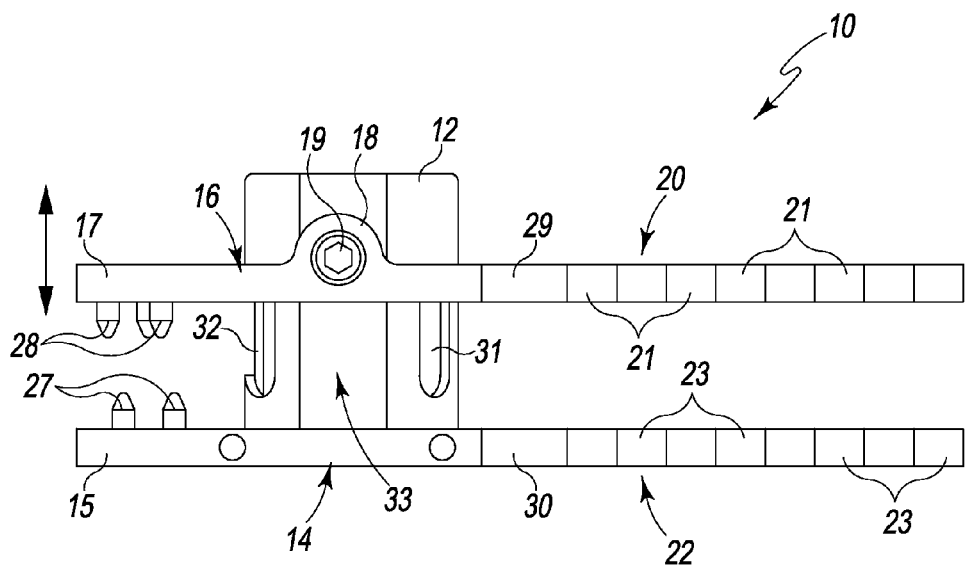
FIG. 1 is a top view of an embodiment of a posterior spinal implant for fixing a lumbar vertebra relative to the sacrum fashioned in accordance with the present principles.
Figure 2:
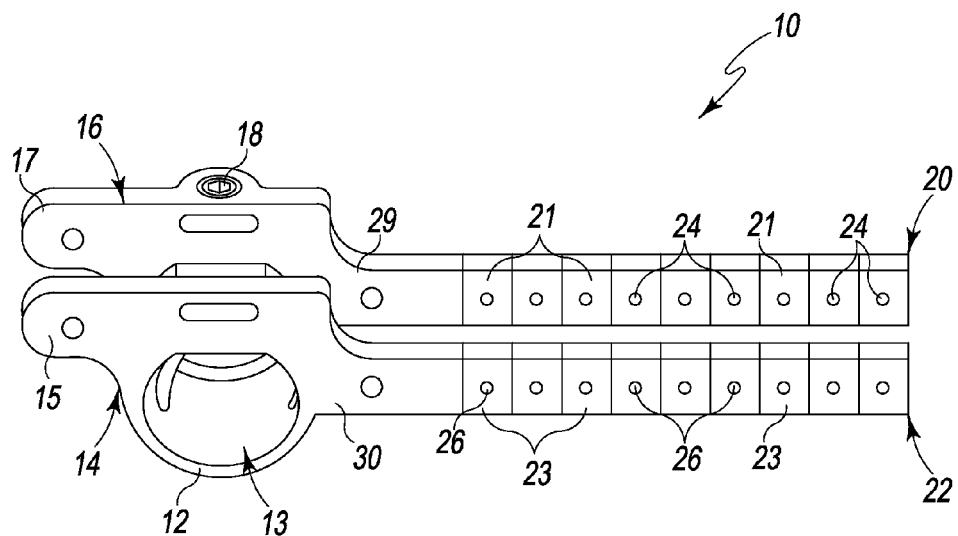
FIG. 2 is an upper side view of the posterior spinal implant of FIG. 1.
Figure 3:
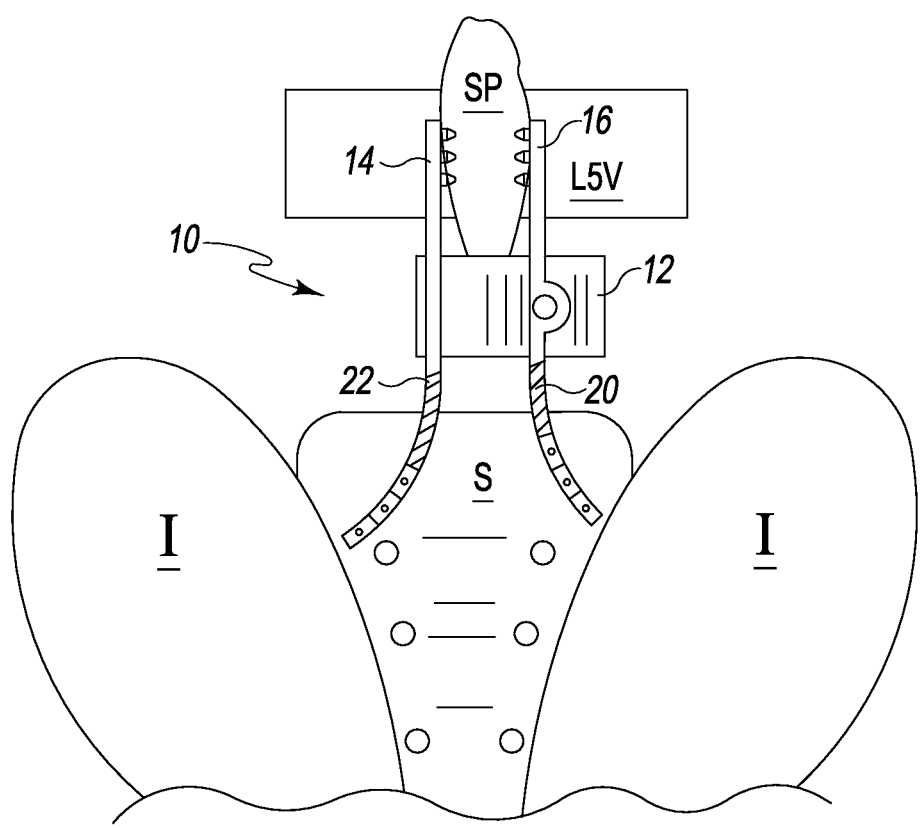
FIG. 3 is a posterior view of the posterior spinal implant of FIG. 1 attached to the spinous process of the L5 vertebra and the sacrum.
Figure 4:
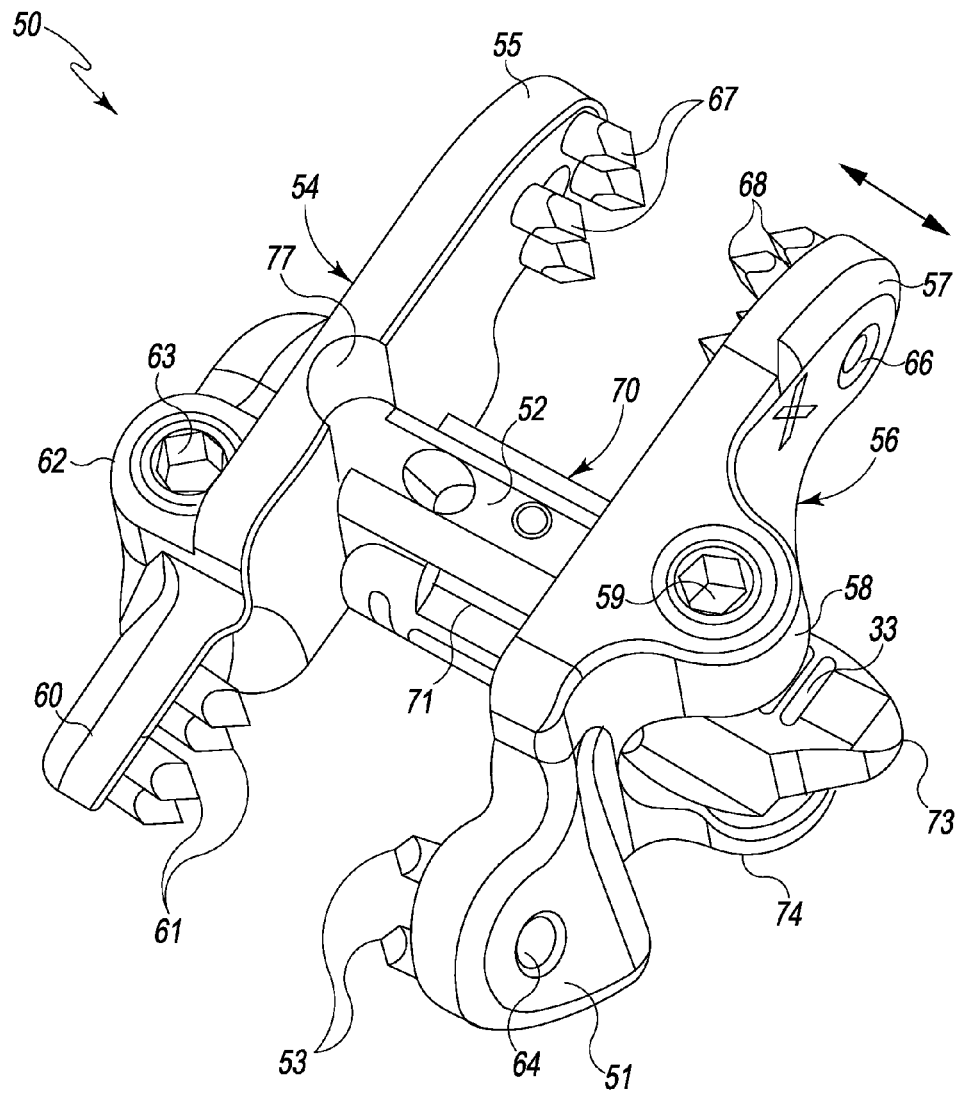
FIG. 4 is a perspective view of another embodiment of a posterior spinal implant for fixing a lumbar vertebra relative to the sacrum fashioned in accordance with the present principles.
Figure 5:
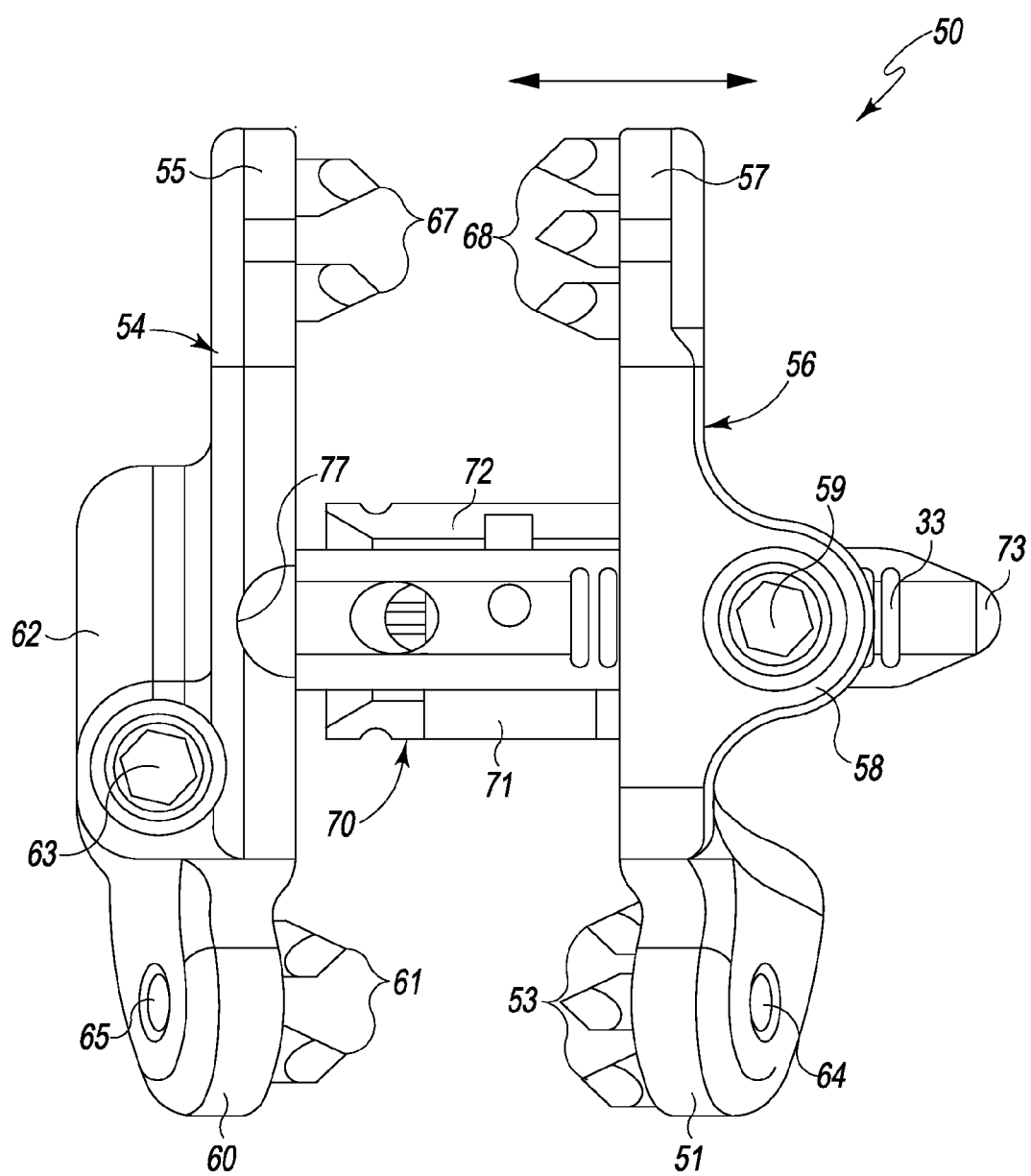
FIG. 5 is a top view of the posterior spinal implant of FIG. 4.
Figure 6:
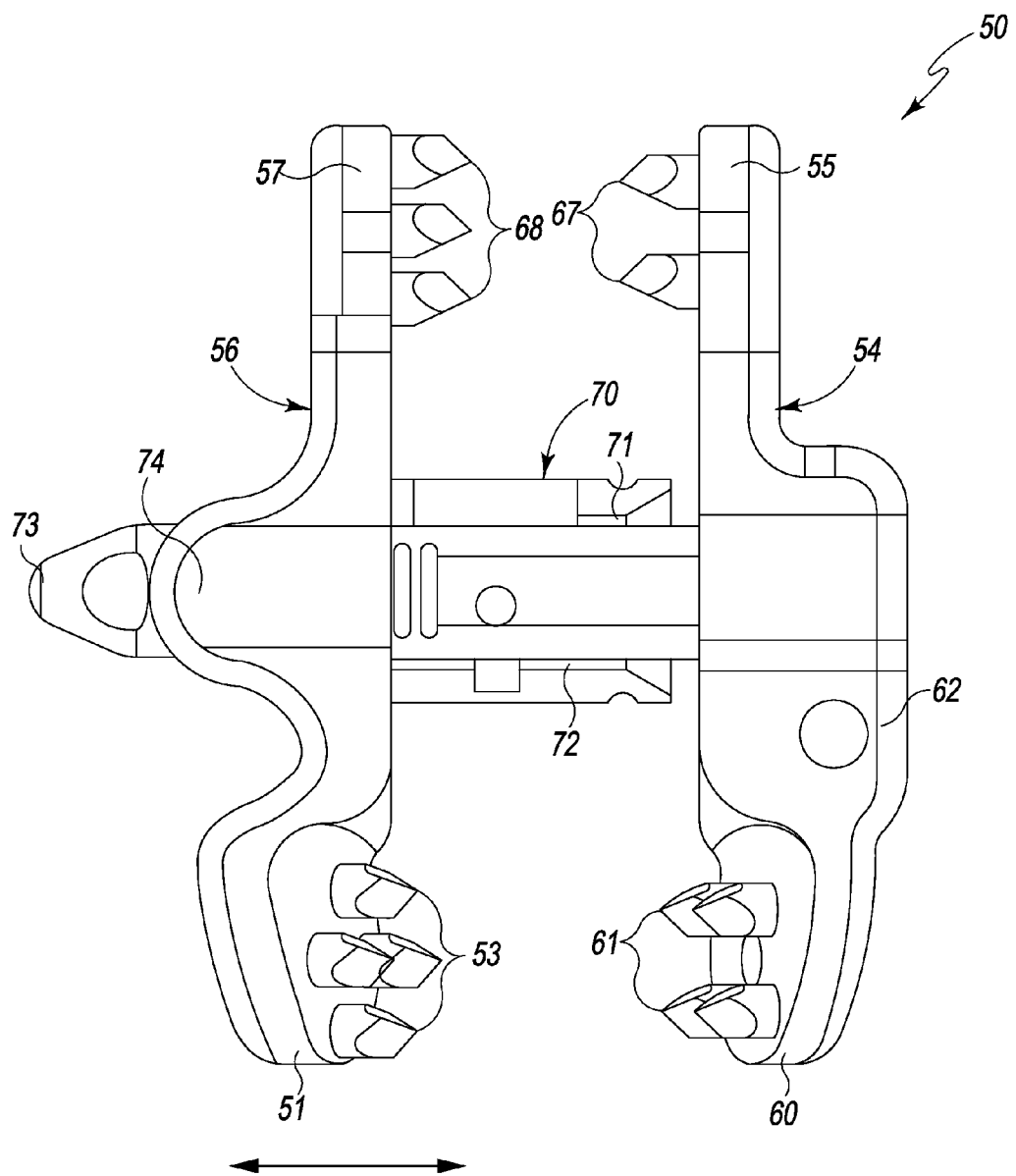
FIG. 6 is a bottom view of the posterior spinal implant of FIG. 4.

Referring to FIGS. 1 and 2, there is depicted two views of an embodiment of a spinal implant for the posterior fixation of a lumbar vertebra to the sacrum, generally designated 10 (posterior spinal implant 10), fashioned in accordance with the present principles. The posterior spinal implant 10 is designed to attach to a spinous process of a lumbar vertebrae and to the sacrum. Particularly, but not necessarily exclusively, the posterior spinal implant 10 is designed to attach to the spinous process of a lower lumbar vertebrae (e.g. the L4 or L5 vertebra) and to the sacrum. Such is seen in FIG. 3 wherein the posterior spinal implant 10 is attached to the spinous process SP of the lower lumbar L5 vertebra L5V and to the sacrum S between the left and right illiums I of the pelvis.

The posterior spinal implant 10 has a body 12 formed as a barrel or tube having a hollow tubular interior 13. A first transverse surface 14 is fixedly disposed on one transverse end of the barrel 12 and includes a first flange 15 extending from a superior end of the first transverse surface 14. As best seen in FIG. 1, the first superior flange 15 has a plurality of spikes or teeth 27 that extend inwardly from an inner surface of the first superior flange 15 and thus are designed to engage or clamp against a spinous process of the lumbar vertebra (i.e. a first transverse surface of the spinous process of the lumbar vertebra). See, for example, FIG. 3.

A first elongated flange, tail, band or strip 22 extends from a nub 30 on an inferior end of the first transverse surface 14. The first inferior tail 22 projects a length or span in the inferior direction and is defined by a plurality of segments 23. The segments 23 are scored or otherwise joined to each other to allow easy removal thereof in order to allow easy sizing of the length or span of the tail 22. Additionally, each segment 23 has a bore 26 for reception of a bone screw (not shown) for attaching the tail 22 to the sacrum S at the particular segment 23 receiving the bone screw. It should be appreciated that each segment 23 may not receive a bone screw and thus may not be attached or affixed to the sacrum. By providing a plurality of segments 23 with bores 26, the surgeon has leeway or options in attachment of the tail 22 to the sacrum.

A second transverse surface 16 is movably disposed on another transverse end of the barrel 12 and includes a second flange 17 extending from a superior end of the second transverse surface 16. As best seen in FIG. 1, the second superior flange 17 has a plurality of spikes or teeth 28 that extend inwardly from an inner surface of the second superior flange 17 and thus are designed to engage or clamp against the spinous process of the lumbar vertebra (i.e. a second transverse surface of the spinous process of the lumbar vertebra). See, for example, FIG. 3.

A second elongated flange, tail, band or strip 20 extends from a nub 29 on an inferior end of the second transverse surface 16. The second inferior tail 20 projects a length or span in the inferior direction and is defined by a plurality of segments 21. The segments 21 are scored or otherwise joined to each other to allow easy removal thereof in order to allow easy sizing of the length or span of the tail 20. Additionally, each segment 21 has a bore 24 for reception of a bone screw (not shown) for attaching the tail 20 to the sacrum S at the particular segment 21 receiving the bone screw. It should be appreciated that each segment 21 may not receive a bone screw and thus may not be attached or affixed to the sacrum. By providing a plurality of segments 21 with bores 24, the surgeon has leeway or options in attachment of the tail 20 to the sacrum.

As indicated above, the first transverse surface 14 is fixed to the barrel 12 while the second transverse surface 16 is movable along the barrel 12 and thus away from and towards the first transverse surface 14 as indicated by the double-headed arrow in FIG. 1. The first superior flange 15 and the first inferior tail 22 are thus fixed relative to the barrel 12, while the second superior flange 17 and the second inferior tail 20 are movable along the barrel 12 and thus away from and towards the first superior flange 15 and the first inferior tail 22. In this manner, the first and second superior flanges 15, 17 and their respective spikes 27, 28 provide clamping against a spinous process of a vertebra.

The barrel 12 includes a first groove 31 on an outer surface of a side thereof and a second channel 32 on the outer surface of another side thereof. The second transverse surface 17 includes projections that fit into the channels 31, 32 in order to retain and prevent rotation of the second transverse surface 17 on the barrel 12. Additionally, the barrel 12 includes a grooved flat 33 that provides stepped demarcations. A boss 18 is provided on the second transverse surface 16 that is positioned over the flat 33 and which holds a set screw 19. In this manner, the second transverse surface 16 may be fixed relative to the barrel 12 after the second transverse surface 16 is properly positioned.

The first and second inferior tails 22, 20 may be bent as necessary in order to properly position them relative to the sacrum for attachment thereof. This allows the wider flat portion of each tail to lie against the sacrum. Thereafter, one or more segments of each tail is affixed or attached to the sacrum via bone screws through their respective segment bore (see FIG. 3).

Referring to FIGS. 4-7, there is depicted various views of another embodiment of a spinal implant for the posterior fixation of a lumbar vertebra to the sacrum, generally designated 50 (posterior spinal implant 50), fashioned in accordance with the present principles. The posterior spinal implant 50 is designed to attach to a spinous process of a lumbar vertebrae and to the sacrum. Particularly, but not necessarily exclusively, the posterior spinal implant 50 is designed to attach to the spinous process of a lower lumbar vertebrae (e.g. the L5 vertebra) and to the sacrum. Such is seen in FIGS. 8-11 wherein the posterior spinal implant 50 is attached to the spinous process SP of the lower lumbar L5 vertebra L5V and to the sacrum S between the left and right illiums I of the pelvis.

The posterior spinal implant 50 has a first member or arm 54 and a second member or arm 56 that is adjustably situated on the first member 54. The first arm 54 has a projection 70 extending transverse to the arm 54. The projection 70 may be adjustable in the anterior/posterior direction as retained in channel 77 of the arm 54. The second arm 56 is movably carried on the projection 70 so that the second arm 56 is adjustable along its length (as indicated by the double-headed arrow). The adjustability of the second arm 56 along the length of the projection 70 and adjusts the distance between the first and second arms 54, 56. This provides a clamp or clamping feature as between the first and second arms 54, 56 to clamp onto or grip against the spinous process on one end thereof (a spinous process attachment portion) and the sacrum at the other end thereof (a sacrum attachment portion).

The first arm 54 has a first superior flange or spinous process segment 55 of the spinous process attachment portion having a plurality of spikes or teeth 67 that extend inwardly from an inner surface of the first spinous process segment 55 which are designed/configured to engage or clamp against a spinous process of the lumbar vertebra (i.e. a first transverse surface of the spinous process of the lumbar vertebra) such as depicted in FIGS. 8-11. The first spinous process segment 55 also may have a bore 69 for receipt of a bone screw (not shown). The optional addition of a bone screw would aid in retention of the first spinous process segment 55 onto the spinous process. The second arm 56 has a second superior flange or spinous process segment 57 of the spinous process attachment portion having a plurality of spikes or teeth 68 that extend inwardly from an inner surface of the second spinous process segment 57 which are designed/configured to engage or clamp against the spinous process of the lumbar vertebra (i.e. a second transverse surface of the spinous process of the lumbar vertebra) as depicted in FIGS. 8-11. The second spinous process segment 57 also may have a bore 66 for receipt of a bone screw (not shown). The optional addition of a bone screw would aid in retention of the second spinous process segment 57 onto the spinous process.

Figure 7:
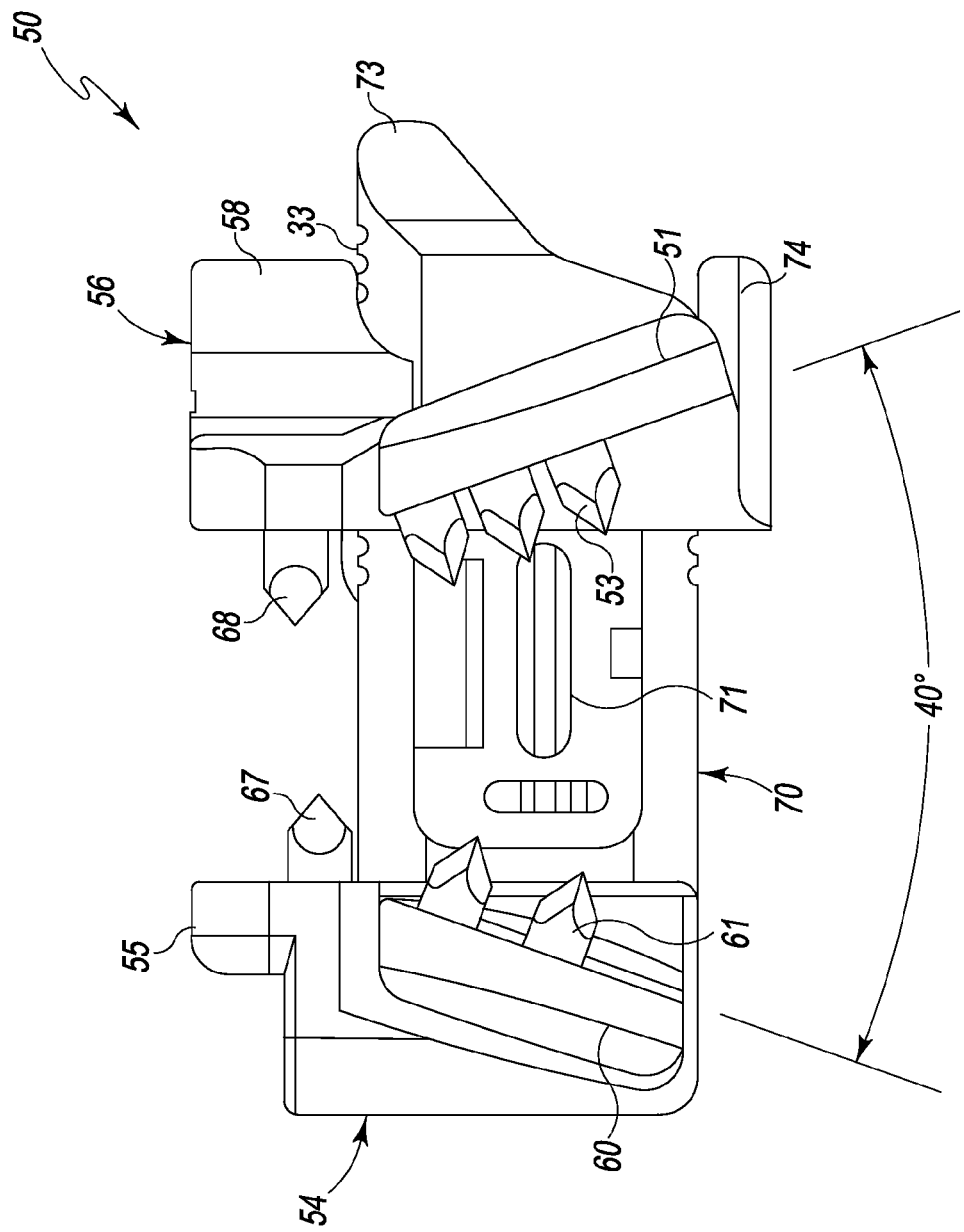
FIG. 7 is an inferior view of the posterior spinal implant of FIG. 4 particularly illustrating angling of the sacrum attachment portion thereof.
Figure 8:
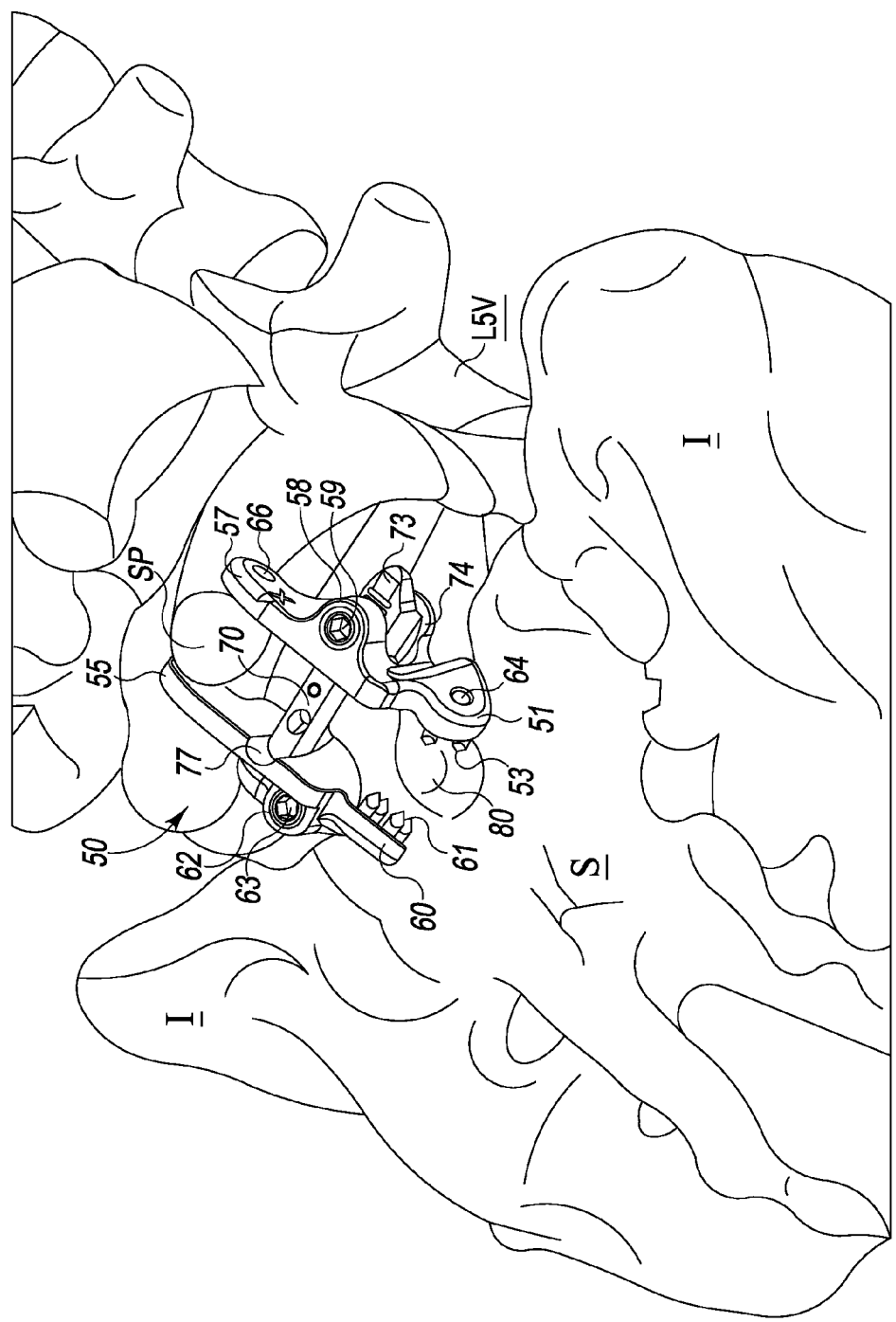
FIG. 8 is an upper, generally lateral side view of the posterior spinal implant of FIG. 4 attached to the spinous process of the L5 vertebra and the sacrum.

The first arm 54 has a first inferior flange or sacrum segment 60 of the sacrum attachment portion having a plurality of spikes or teeth 61 that extend generally inwardly and downwardly from an inner surface of the first sacrum segment 60 which are designed/configured to engage or clamp against a sacrum (i.e. a transverse side/surface of the protuberance 80 of the sacrum) such as depicted in FIGS. 8-11. The second arm 56 has a second inferior flange or sacrum segment 51 of the sacrum attachment portion having a plurality of spikes or teeth 53 that extend generally inwardly and downwardly from an inner surface of the second sacrum segment 51 which are designed/configured to engage or clamp against the sacrum (i.e. another transverse side/surface of the protuberance 80 of the sacrum) such as depicted in FIGS. 8-11. As best shown in FIG. 7, the first and second sacrum segments 60, 51 are angled downwardly providing a 40° angle between them, off of perpendicular.

The first sacrum segment 60 also may have a bore 65 for receipt of a bone screw (not shown). The optional addition of a bone screw would aid in retention of the first sacrum segment 55 onto the sacrum. Likewise, the second sacrum segment 51 also may have a bore 64 for receipt of a bone screw (not shown). The optional addition of a bone screw would aid in retention of the second sacrum segment 51 onto the sacrum.

Figure 9:
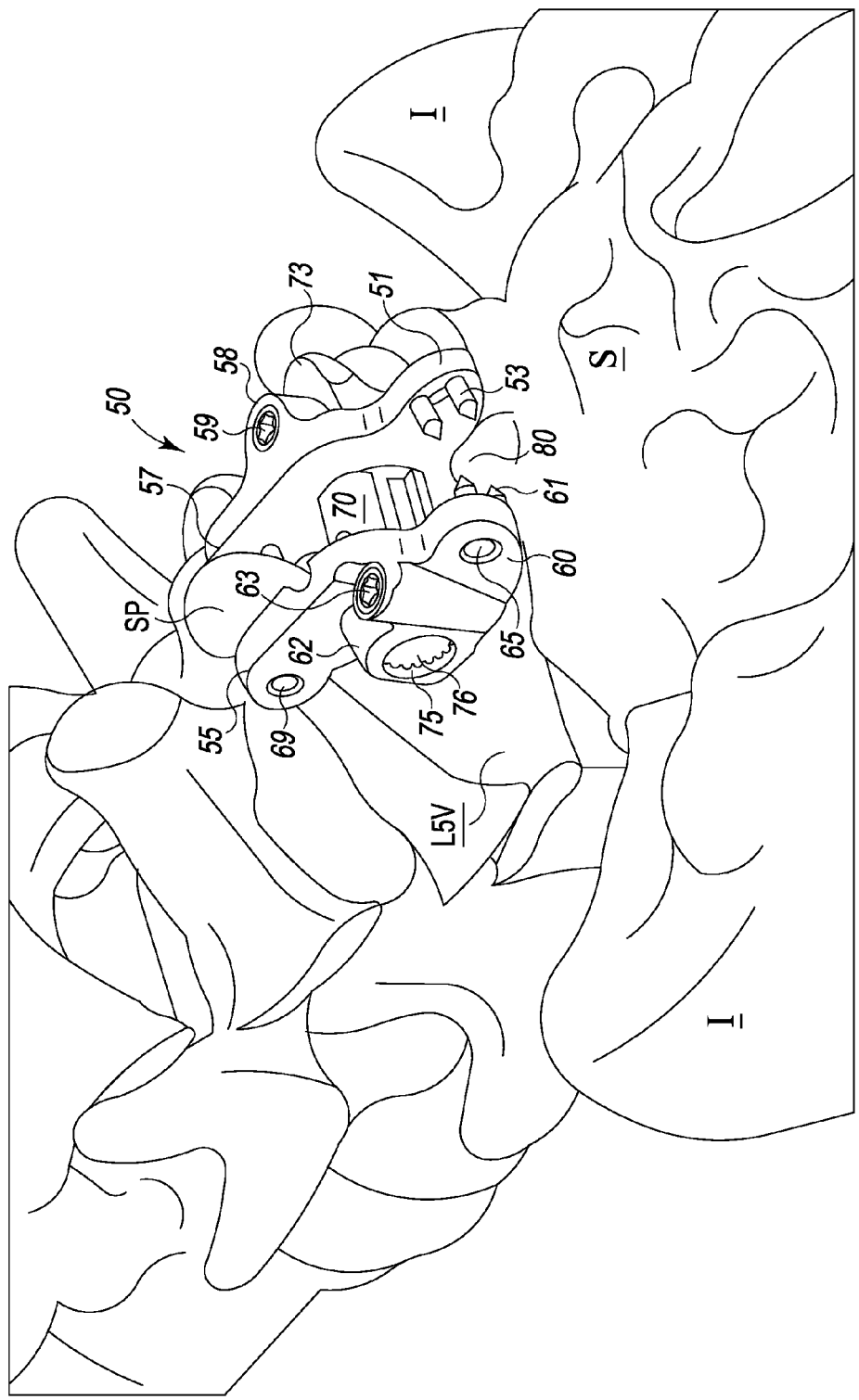
FIG. 9 is an upper, generally medial side view of the posterior spinal implant of FIG. 4 attached to the spinous process of the L5 vertebra and the sacrum.
Figure 10:
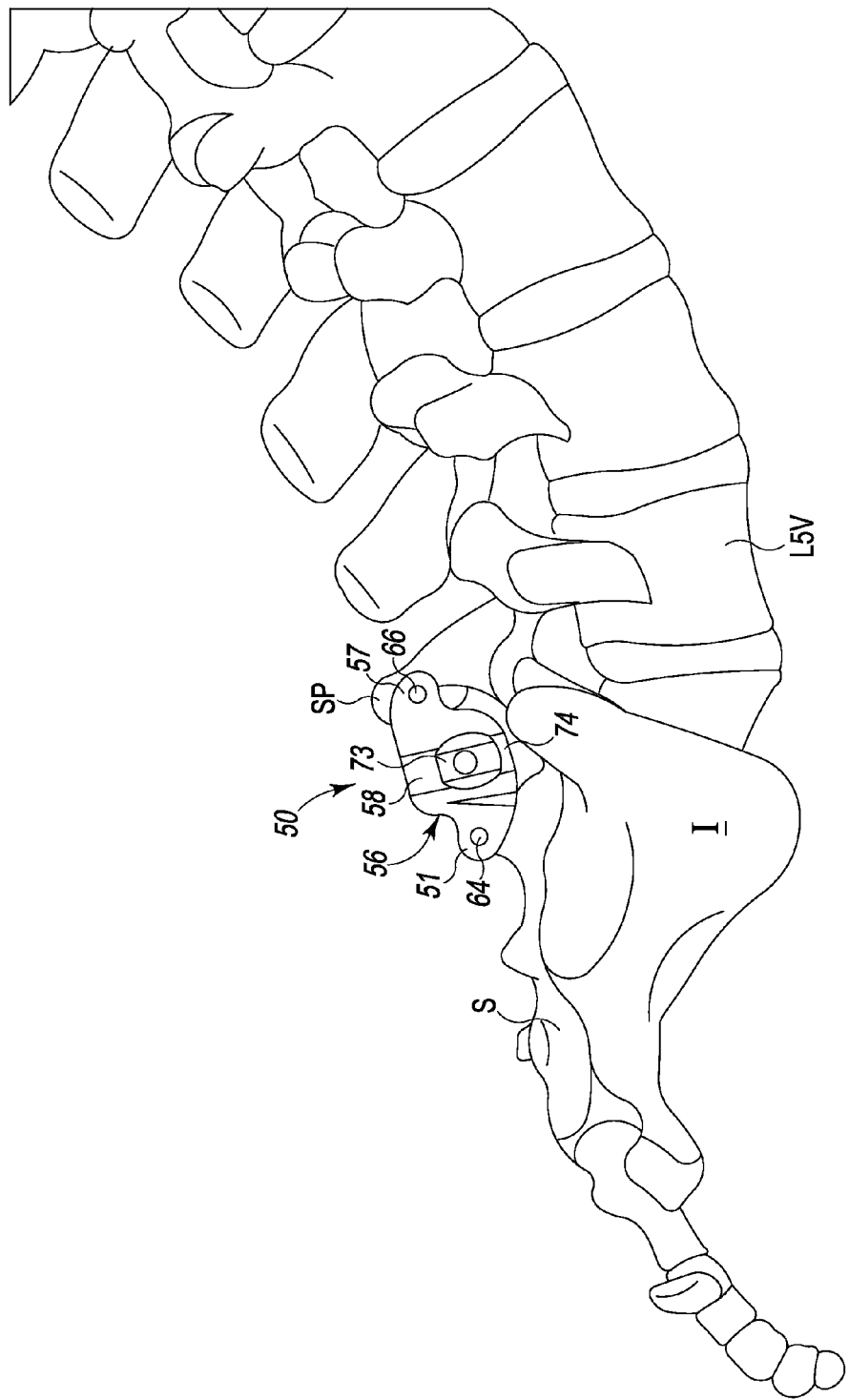
FIG. 10 is a lateral side view of the posterior spinal implant of FIG. 4 attached to the spinous process of the L5 vertebra and the sacrum.
Figure 11:
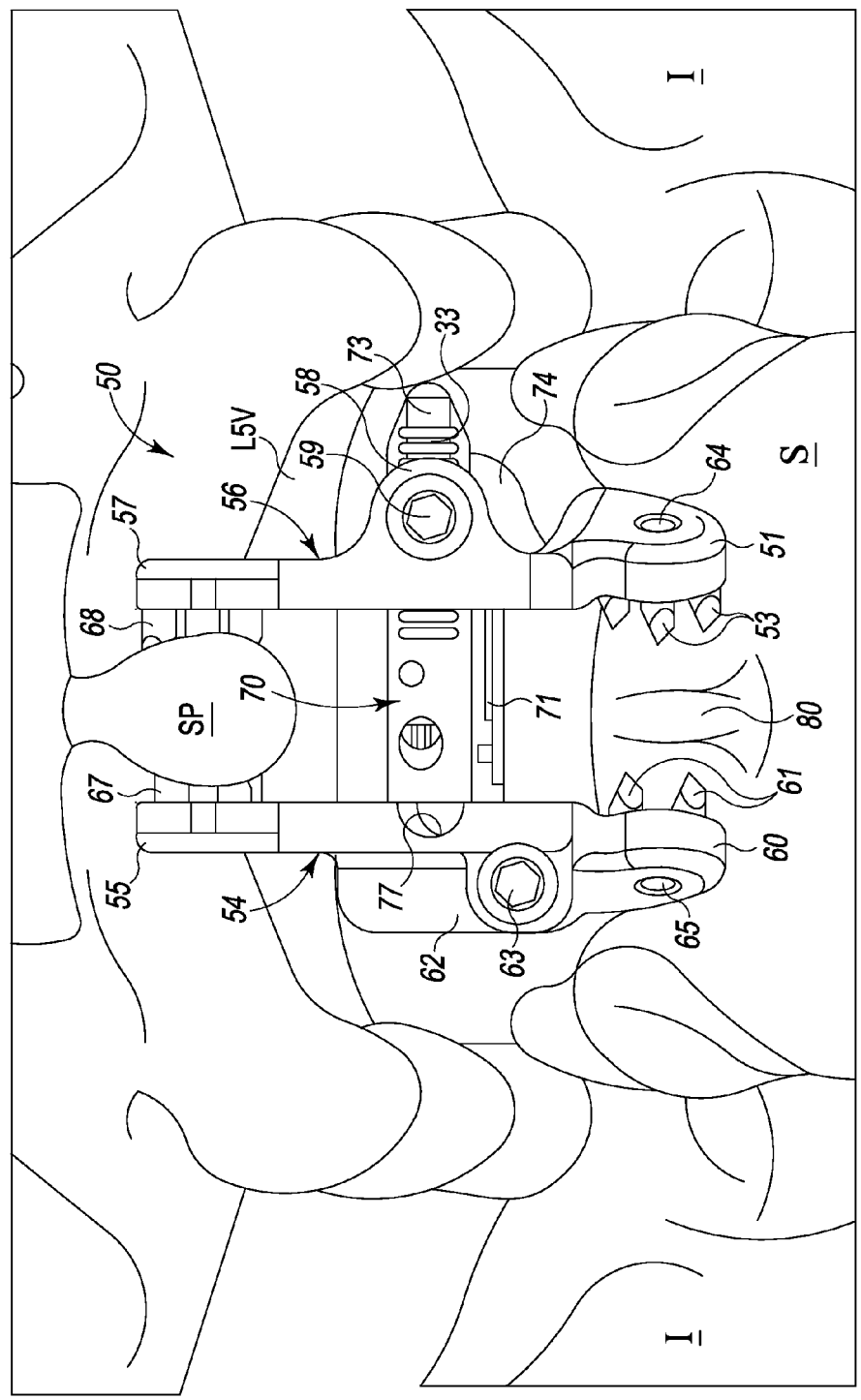
FIG. 11 is a posterior view of the posterior spinal implant of FIG. 4 attached to the spinous process of the L5 vertebra and the sacrum.

The first arm 54 is fixed to the projection 70 in a transverse direction, but able to rotation relative thereto. As best seen in FIG. 9, an end 76 of the projection 70 is situated in a bore 75 of a boss 62 of the first arm 54. This allows the first arm 54 to rotate about the projection 70. The end 76 has peripheral teeth that allow the first arm 54 to be fixed in rotational position relative to the projection 70 via a set screw 63 situated in the boss 62.

As indicated above, the second arm 56 is movable along the projection 70 and thus relative to the first arm 54. This allows the first and second arms 54, 56 and thus the first and second spinous process segments 55, 57 of the spinous process attachment portion and the first and second sacrum segments 60, 51 of the sacrum attachment portion to clamp against the spinous process SP of the lumbar vertebra L5V and the sacrum protuberance 80 of the sacrum S, and to adapt to variations in individual anatomy. The second arm 56 has a bore therein with a transverse extending ledge 74 through which the projection 70 extends. The projection has first and second channels 71, 72 that allow the second arm 56 to be guided along the projection 70. The top surface 52 of the projection 70 has a plurality of grooves or notches 33 that extend to an end 73 of the projection. The second arm 56 has a boss 58 which holds a set screw 59. The set screw 59 in conjunction with the grooves 33 allows the second arm 56 to be fixed in position relative to the projection 70.

Figure 12:
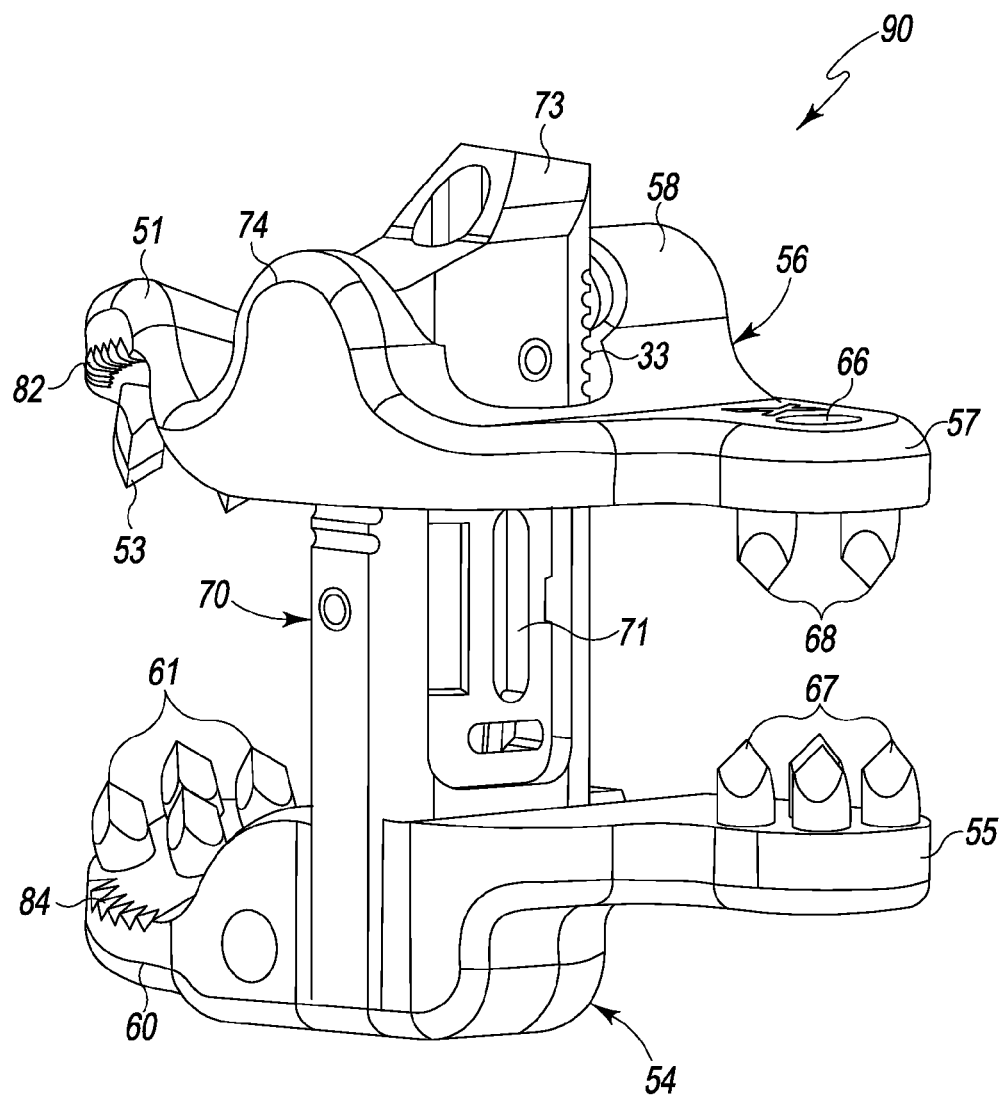
FIG. 12 is a perspective view of another embodiment of a posterior spinal implant for fixing a lumbar vertebra relative to the sacrum fashioned in accordance with the present principles.
Figure 13:
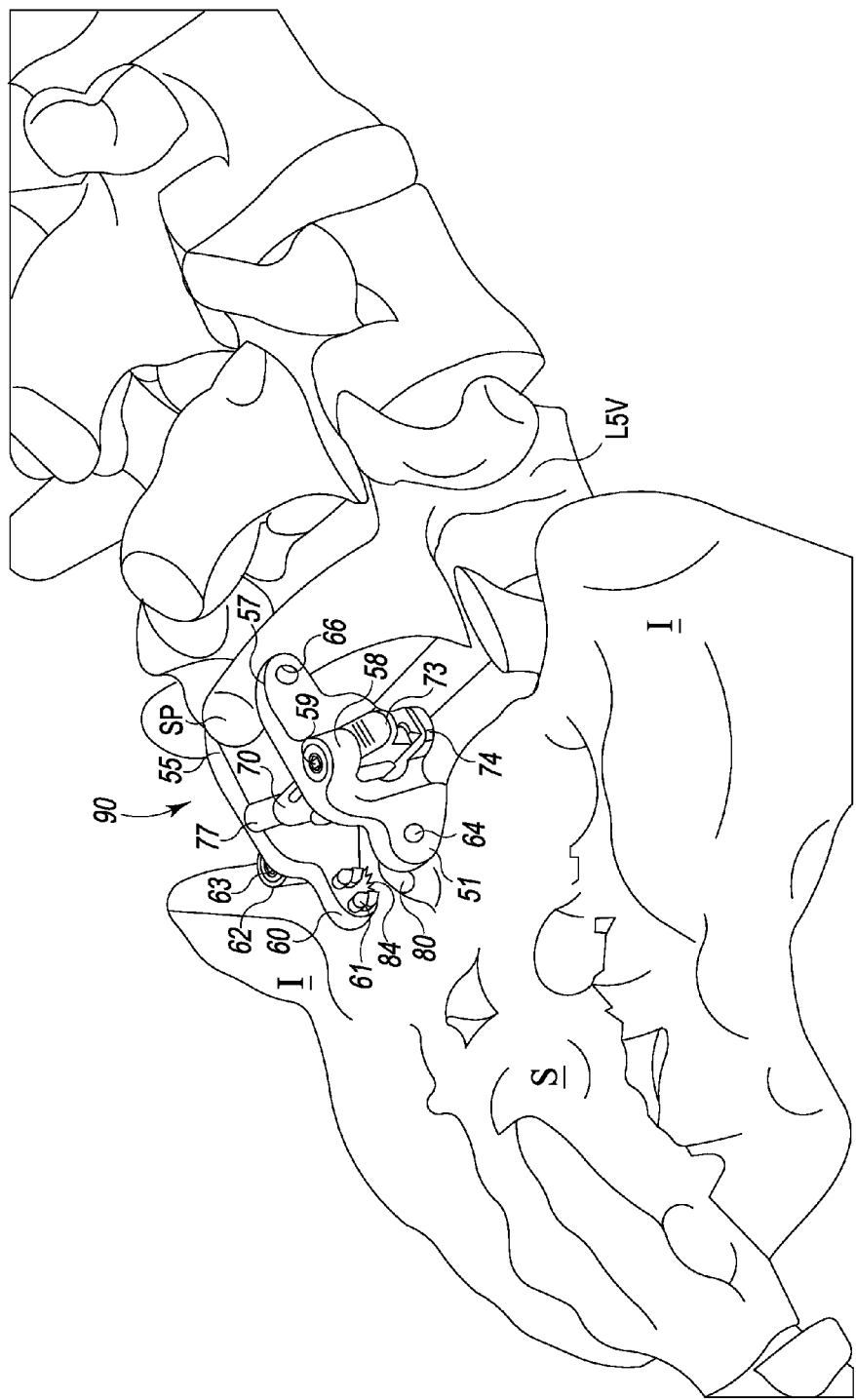
FIG. 13 is an upper, generally lateral side view of the posterior spinal implant of FIG. 12 attached to the spinous process of the L5 vertebra and the sacrum.
Figure 14:
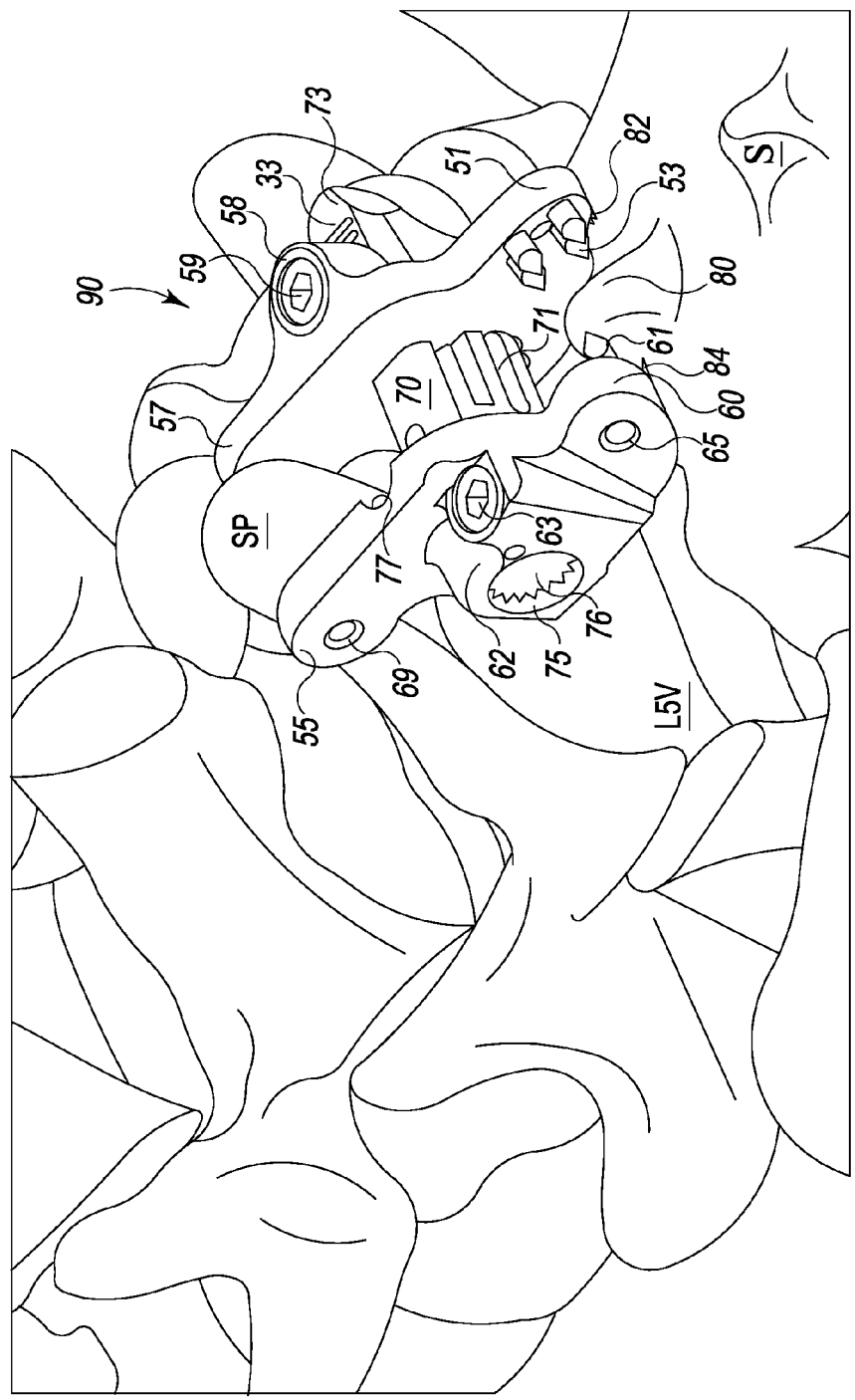
FIG. 14 is an upper, generally medial side view of the posterior spinal implant of FIG. 12 attached to the spinous process of the L5 vertebra and the sacrum.
Figure 15:
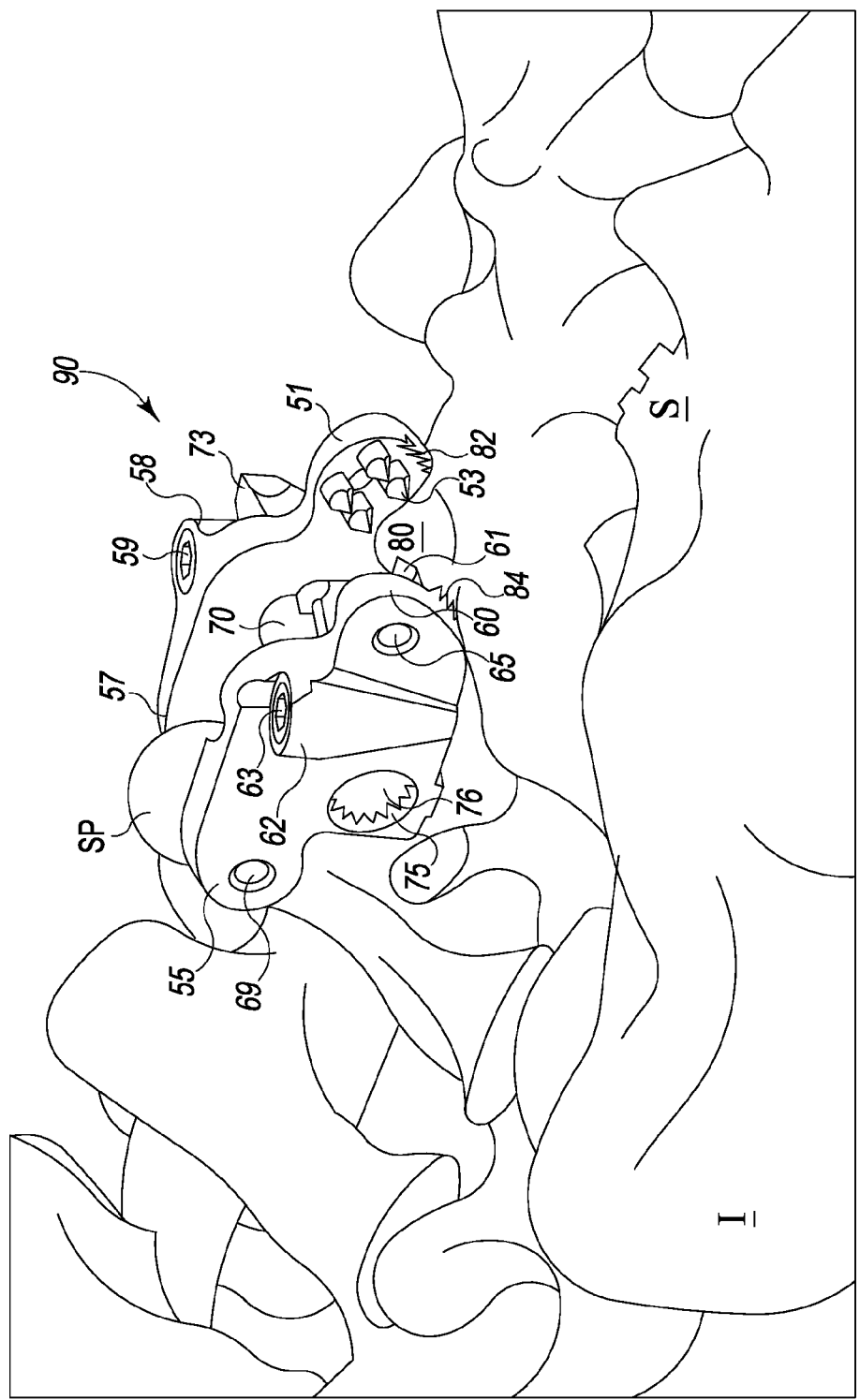
FIG. 15 a generally medial side view of the posterior spinal implant of FIG. 12 attached to the spinous process of the L5 vertebra and the sacrum.
Figure 16:
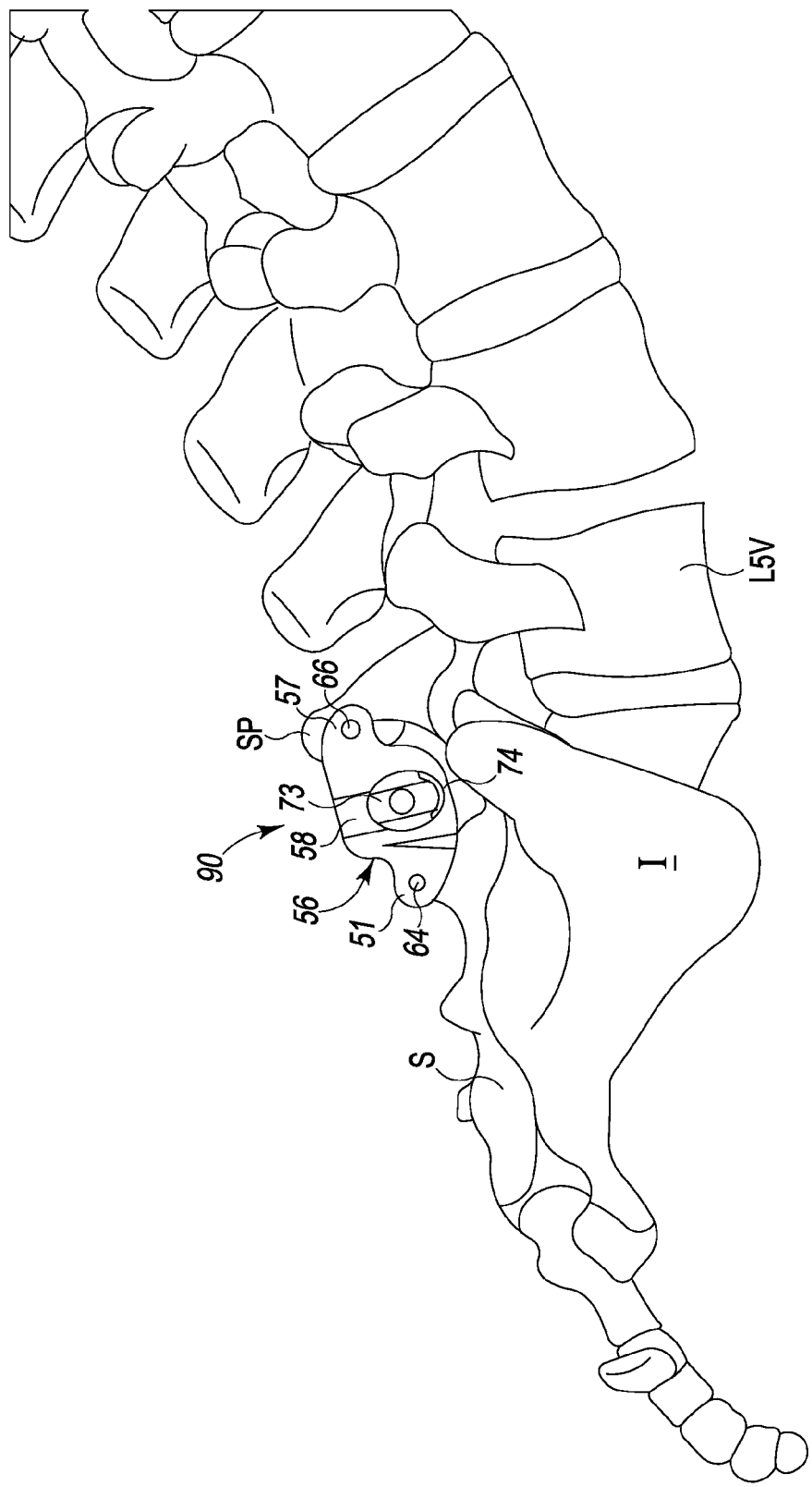
FIG. 16 is a lateral side view of the posterior spinal implant of FIG. 12 attached to the spinous process of the L5 vertebra and the sacrum.
Figure 17:
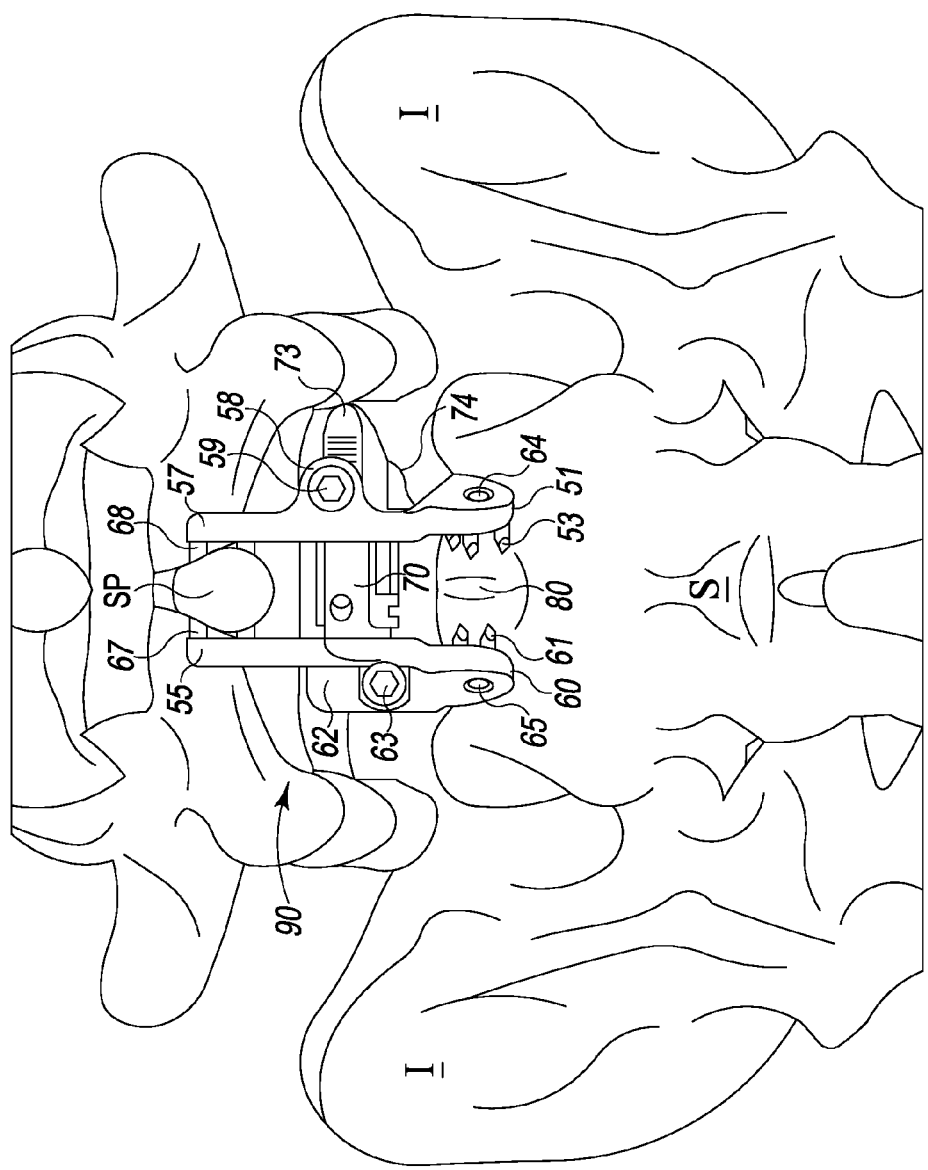
FIG. 17 is an inferior/posterior view of the posterior spinal implant of FIG. 12 attached to the spinous process of the L5 vertebra and the sacrum.

FIG. 12 depicts a spinal implant 90 having a minor variation to the spinal implant 50. Particularly, the spinal implant 90 includes a first set of teeth ("fish teeth") or the like 84 on a lower edge of the first sacrum segment 60 of the first arm 54. Likewise, the spinal implant 90 includes a second set of teeth ("fish teeth") or the like 82 on a lower edge of the second sacrum segment 51 of the second arm 56. The teeth 82, 84 provide extra gripping or clamping against the protuberance 80 of the sacrum. The spinal implant 90 is depicted in various views in FIGS. 13-17 affixed to the spinous process SP of the lumbar vertebra L5V and the protuberance 80 of the sacrum S.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal implant comprising:
   a first arm having a first spinous process segment of a spinous process clamp for attachment to a spinous process of a lumbar vertebra on a superior end thereof and a first sacrum segment of a sacrum clamp for attachment to a protuberance of a sacrum on an inferior end thereof;
   a second arm having a second spinous process segment of the spinous process clamp on a superior end thereof and a second sacrum segment of the sacrum clamp on an inferior end thereof; and
   a projection fixed to the first arm and extending transverse thereto, the second arm movably disposed on the projection for length adjustment between the first and second spinous process segments for attachment of the spinous process clamp to the spinous process of the lumbar vertebra, and between the first and second sacrum segments for concerted attachment of the sacrum clamp to the protuberance of the sacrum;
   wherein the first spinous process segment includes an inner surface being generally parallel to an inner surface of the second spinous process segment; and
   wherein the first sacrum segment includes an inner surface that angles away from an inner surface of the second sacrum segment.

2. The spinal implant of claim 1, wherein:
   the first spinous process segment has a plurality of laterally extending spikes for contact with one side of the spinous process;
   the second spinous process segment has a plurality of laterally extending spikes for contact with another side of the spinous process;
   the first sacrum segment has a plurality of laterally extending spikes for contact with one side of the protuberance of the sacrum; and
   the second sacrum segment has a plurality of laterally extending spikes for contact with another side of the protuberance of the sacrum.

3. The spinal implant of claim 2, further comprising:
   a first set of teeth disposed on an edge of the first sacrum segment; and
   a second set of teeth disposed on an edge of the second sacrum segment.

4. The spinal implant of claim 2, wherein the second arm includes a set screw for fixing position of the second arm on the projection.

5. The spinal implant of claim 2, wherein the first arm is rotatable relative to the projection.

6. The spinal implant of claim 2, wherein:
   the first sacrum segment is angled relative to a superior to inferior plane; and
   the second sacrum segment is angled relative to the superior to inferior plane.

7. The spinal implant of claim 6, wherein:
   the laterally extending spikes on the first sacrum segment project from the inner surface of the first sacrum segment, the inner surface angled in a medial direction; and
   the laterally extending spikes on the second sacrum segment project from the inner surface of the second sacrum segment, the inner surface angled in a lateral direction.

8. A spinal implant comprising:
   a first arm having a first spinous process segment of a spinous process clamp for attachment to a spinous process of a lumbar vertebra on a superior end thereof and a first sacrum segment of a sacrum securement for attachment to a sacrum on an inferior end thereof;
   a second arm having a second spinous process segment of the spinous process clamp on a superior end thereof and a second sacrum segment of the sacrum securement on an inferior end thereof; and
   a projection fixed to the first arm and extending transverse thereto, the second arm movably disposed on the projection for length adjustment between the first and second spinous process segments for attachment of the spinous process clamp to the spinous process of the lumbar vertebra, and between the first and second sacrum segments for attachment of the sacrum securement to the sacrum;
   wherein the first sacrum segment includes a first flexible strip defining a first generally planar surface, the first generally planar surface including a first plurality of detachable segments; and
   wherein the second sacrum segment includes a second flexible strip defining a second generally planar surface, the second generally planar surface including a second plurality of detachable segments.

9. The spinal implant of claim 8, wherein:
   the first spinous process segment has a plurality of laterally extending spikes for contact with one side of the spinous process; and
   the second spinous process segment has a plurality of laterally extending spikes for contact with another side of the spinous process.

10. The spinal implant of claim 9; wherein:
each detachable segment of the first plurality of detachable segments has a bore therethrough; and
each detachable segment of the second plurality of detachable segments has a bore therethrough.

11. A spinal implant comprising:
a first superior to inferior member having a first spinous process segment of a spinous process clamp for attachment to a spinous process of a lumbar vertebra on a superior end thereof and a first sacrum segment of a sacrum clamp for attachment to a protuberance of a sacrum on an inferior end thereof;
a second superior to inferior member having a second spinous process segment of the spinous process clamp on a superior end thereof and a second sacrum segment of the sacrum clamp on an inferior end thereof; and
a projection fixed to the first superior to inferior member and extending transverse thereto, the second superior to inferior member movably disposed on the projection for length adjustment between the first and second spinous process segments for attachment of the spinous process clamp to the spinous process of the lumbar vertebra, and between the first and second sacrum segments for concerted attachment of the sacrum clamp to the protuberance of the sacrum;
wherein the first spinous process segment includes an inner surface being generally parallel to an inferior-superior plane; and
wherein the first sacrum segment includes an inner surface being angled relative to the inferior-superior plane.

12. The spinal implant of claim 11, wherein:
the first spinous process segment has a plurality of spikes projecting from the inner surface thereof for contact with one side of the spinous process;
the second spinous process segment has a plurality of spikes projecting from the inner surface thereof for contact with another side of the spinous process;
the first sacrum segment has a plurality of spikes projecting from the inner surface thereof for contact with one side of the protuberance of the sacrum; and
the second sacrum segment has a plurality of spikes projecting from the inner surface thereof for contact with another side of the protuberance of the sacrum.

13. The spinal implant of claim 12, further comprising:
a first set of teeth disposed on an edge of the first sacrum segment; and
a second set of teeth disposed on an edge of the second sacrum segment.

14. The spinal implant of claim 12, wherein the second superior to inferior member includes a set screw for fixing position of the second superior to inferior member on the projection.

15. The spinal implant of claim 12, wherein:
the first sacrum segment is angled relative to a superior to inferior plane; and
the second sacrum segment is angled relative to the superior to inferior plane.

16. The spinal implant of claim 12, wherein the first superior to inferior member is rotatable relative to the projection.

17. The spinal implant of claim 11, wherein the second spinous process segment includes an inner surface being generally parallel to the inferior-superior plane; and
wherein the second sacrum segment includes an inner surface being angled relative to the inferior-superior plane.

* * * * *